United States Patent [19]

Volk

[11] Patent Number: 4,934,809
[45] Date of Patent: Jun. 19, 1990

[54] LENS POSITIONING DEVICE FOR INDIRECT BIOMICROSCOPY OF THE EYE

[76] Inventor: Donald A. Volk, 6805 Mayfield Rd., Apt. 1019, Mayfield Heights, Ohio 44124

[21] Appl. No.: 211,353

[22] Filed: Jun. 24, 1988

[51] Int. Cl.$^5$ ............................................. A61B 3/10
[52] U.S. Cl. .................................... 351/205; 351/214
[58] Field of Search ............... 351/205, 214, 206, 245

[56] References Cited

U.S. PATENT DOCUMENTS 4,504,129 3/1985 Van Iderstine ..................... 351/214

OTHER PUBLICATIONS

Emarah, "Simplified Indirect Ophthalmoscope" British Journal of Ophthalmology, vol. 48, No. 3, 3/64.

*Primary Examiner*—Rodney B. Bovernick
*Attorney, Agent, or Firm*—Baldwin, Egan & Fetzer

[57] ABSTRACT

A lens positioning device for indirect biomicroscopy of a patient's eye and which is adapted to mount a condensing lens in readily adjustable relationship to the patient's eye, for evaluation of for instance the fundus of the eye with the biomicroscope, and with the device being adapted to be readily attached to one of the chin rest vertical bars of the slit lamp biomicroscope. The device comprises a plurality of movable arms for positioning of the lens relative to the eye, with adjustable fasteners for selectively tightening or loosening the tension thereof and thus the resistance to pivotal movement of the arms relative to one another, so as to be able to selectively increase or decrease the resistance to relative movement between the arms, to accommodate the particular desires of the examiner. Once the device is positioned by the examiner to obtain the desired position of the lens relative to the eye of the patient, the lens remains in such position and frees the hand of the examiner to manipulate the slit lamp biomicroscope.

11 Claims, 2 Drawing Sheets

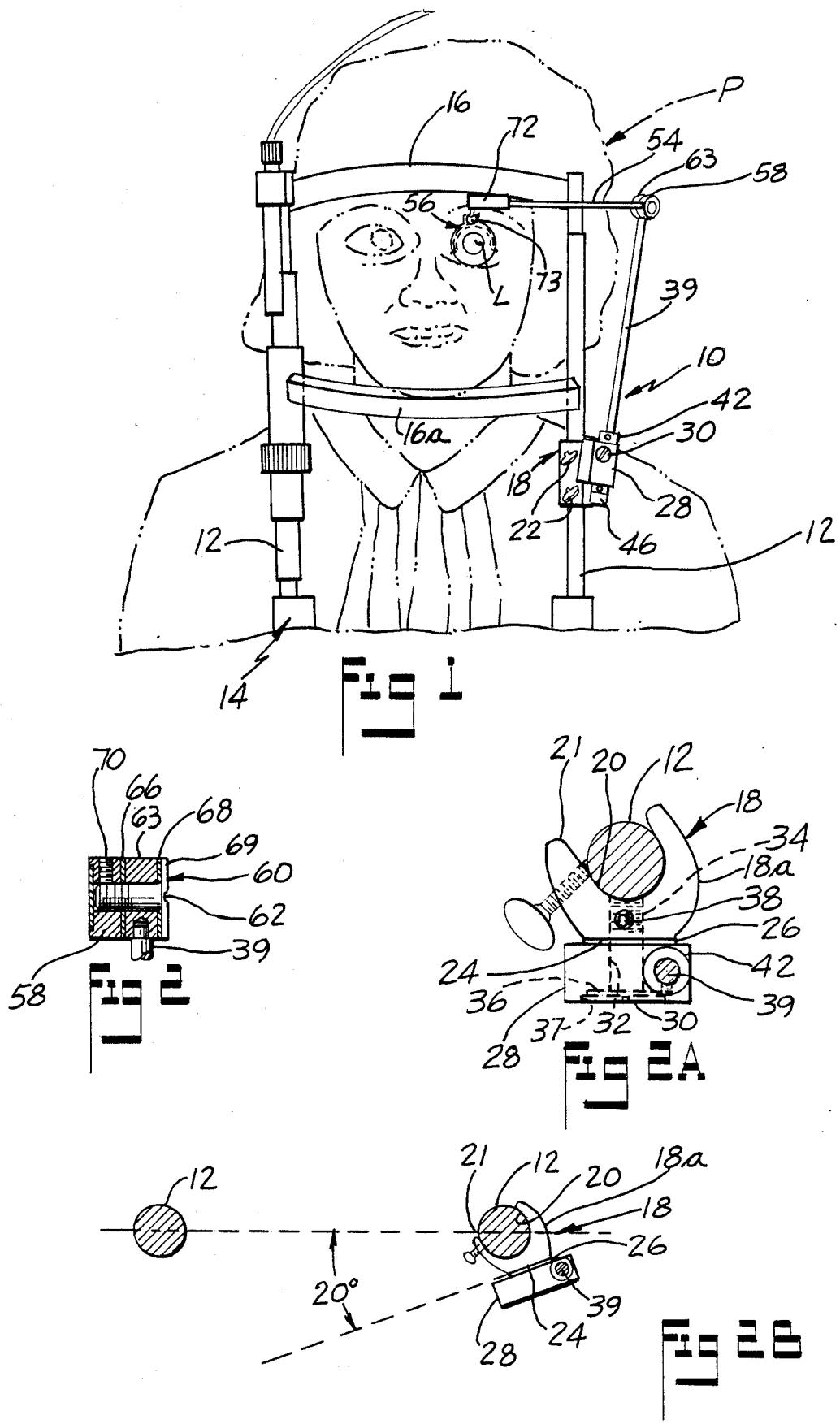

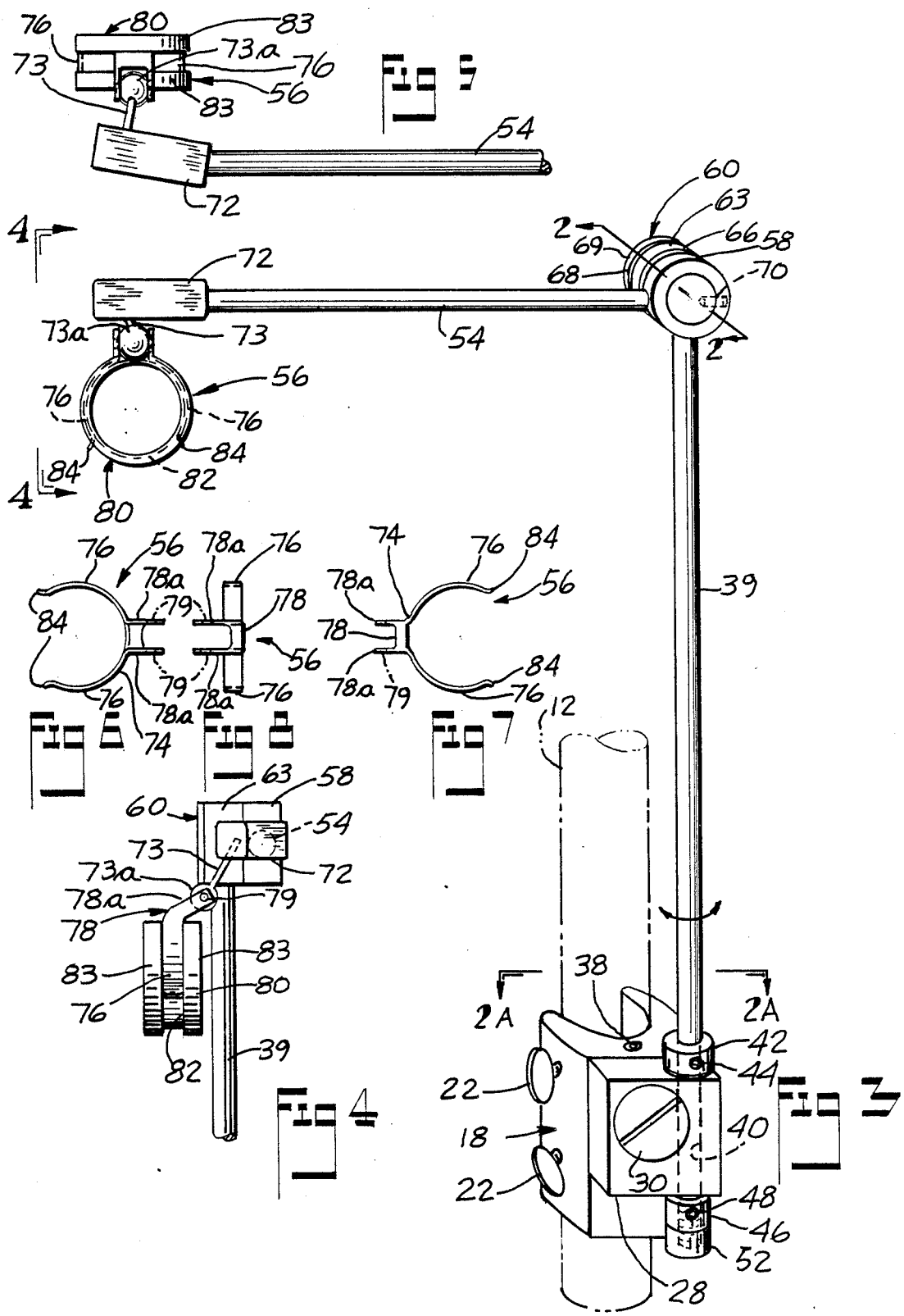

LENS POSITIONING DEVICE FOR INDIRECT BIOMICROSCOPY OF THE EYE

This invention relates in general to lens positioning devices for indirect biomicroscopy of the eye, and more particularly relates to a lens positioning device which is adapted for mounting on one of the chin rest vertical bars of a slit lamp biomicroscope, and which provides for expeditious positioning of a lens realtive to the eye of a patient, and which is adapted to remain in the examiner selected position, and which eliminates the need for manually holding or positioning a lens relative to the patient's eye, during operation of the slit lamp biomicroscope.

BACKGROUND OF THE INVENTION

It is known in the prior art for the examiner or practitioner to manually hold a condensing lens with respect to the patient's eye during funduscopic examination utilizing a slit lamp biomicroscope, and such is conventional procedure utilized by many opticians.

It is also known in the prior art to utilize a mechanical holder for positioning a lens relative to the patient's eye. Such a holder has been attached to the head rest of a slit lamp biomicroscope, and is adapted to position a lens relative to the patient's eye, thus freeing the examiner's hands to hold an eye lid of the patient in position, or to position a fixation target. In such prior art mechanical, manually operated holders, the lens is attached to an articulated lens holder device by glue or some other permanent means, for fastening the lens to the articulated arm of the holder, and thus the lens is not readily movable or adjustable relative to the patient's eye, nor is the lens able to be readily changed if such is determined to be desirable or necessary.

SUMMARY OF THE INVENTION

The present invention provides a lens positioning or holding device which can be readily attached to a slit lamp biomicroscope, and particularly to a chin rest vertical bar thereof, and which can be expeditiously manually adjusted, or moved, by the operator examiner, so as to readily position the associated lens in proper and selected relationship to the eye of the patient, and wherein the lens will remain in its placed position without further holding or adjusting effort on the part of the operator-examiner, and wherein a lens can be readily inserted into and removed from the positioning or holding device.

Accordingly, an object of the invention is to provide a novel lens positioning device adapted for use in indirect biomicroscopy of the eye.

Another object of the invention is to provide a lens positioning device of the latter type which is readily attachable to and removable from a chin rest vertical bar of a slit lamp biomicroscope.

A still further object of the invention is to provide a device of the latter described type which is readily movable relative to the vertical chin rest bar so as to adapt the device to different ages of patient, and to different dimensions of the facial features of patients, so that a condensing lens can be expeditiously positioned relative to the eye of the patient, and held in its selected position relative to such eye, thus freeing the practitioner's hands for other purposes in conjunction with the biomicroscope examination.

Another object of the invention is to provide a lens positioning device of the aforementioned type which includes clamp means for removably attaching the device to a chin rest vertical bar of a slit lamp biomicroscope, with an arm extending upwardly from the clamp means and being rotatable relative thereto about the arm's lengthwise axis, together with means for pivoting the arm in a general vertical plane relative to the clamp means, and with another arm extending laterally of the first arm and pivoted thereto, with the other arm having a lens retaining means mounted thereon adapted to receive a condensing lens, with the lens retaining means being supported by the other arm and movably coupled thereto, for enabling ready manual positioning of the lens retaining means and an associated lens, relative to the other arm, and with the lens retaining means including means operative to cause the lens retaining means to remain where positioned by the operator-examiner, and relative to the other arm.

A still further object of the invention is to provide a lens positioning device of the aforementioned type wherein there is provided a ball and wherein the means operative to cause the lens retaining means to remain where positioned comprises a socket receiving the ball therein in predetermined frictional relationship, thus causing the lens holder to remain in its placed position relative to the patient's eye without need for further handling by the operator-examiner, and wherein the ball and coacting socket are readily disengageable from one another so as to be able to readily separate the lens holder from the supporting arm of the positioning device, but wherein the ball and socket are just as readily reengageable with one another, to remount the lens holder on its supporting arm.

A still further object of the invention is to provide a device of the latter described type which includes means for selectively adjusting the tension at the pivotal joints thereof so as to be able to expeditiously adjust the resistance to relative movement of the arms of the device relative to the base and relative to one another, whereby such resistance to movement can be adjusted to the selected preference of the operator-examiner, together with means for locking in the selected adjustment tension upon the selection thereof.

Other objects and advantages of the invention will be apparent from the following description taken in conjunction with the accompanying drawings wherein:

BRIEF DESCRIPTION OF THE DRAWINGS

FIG. 1 is a diagrammatic, elevational illustration of the lens positioning device of the invention as detachably mounted on one of the vertical chin rest bars of a biomicroscope, and positioning a lens mounted on the positioning device relative to an eye of a patient;

FIG. 2 is a sectional view taken generally along the plane of 2—2 of FIG. 3, looking in the direction of the arrows, and illustrating means for pivoting the arms of the lens positioning device relative to one another and for adjusting the tension and thus the resistance to relative movement between the arms of the lens positioning device, and for locking in such selected tension; the FIG. 2 illustration of structure has been rotated 180° from its position as illustrated in FIG. 3;

FIG. 2A is a sectional view taken generally along the plane of line 2A—2A of FIG. 3, looking in the direction of the arrows, and illustrating the coupling of the lens positioning device to one of the vertical bars of the chin rest of a slit lamp biomicroscope;

FIG. 2B is a diagrammatic fragmentary top plan illustration of a preferred angular relationship of the lens positioning device of the invention relative to its supporting vertical bar of the chin rest of a biomicroscope;

FIG. 3 is an enlarged perspective view of the lens positioning device of the invention as mounted on its supporting chin rest vertical bar (shown in phantom) of a slit lamp biomicroscope, and illustrating the holding or positioning of a lens by the resilient split collar or lens retaining means of the lens positioning device;

FIG. 4 is a fragmentary view taken generally along the plane of line 4—4 of FIG. 3 looking in the direction of the arrows;

FIG. 5 is a fragmentary top plan view of the lens retaining portion of the positioning device of FIG. 3;

FIG. 6 is an elevational view of the lens retaining member of the lens positioning device, as taken from the lefthand side of the FIG. 8 illustration;

FIG. 7 is an elevational view of the lens retaining member of the positioning device, as taken from the righthand side of the FIG. 8 illustration; and FIG. 8 is a top plan view of the lens retaining member of the positioning device as taken from the top of the FIG. 5 illustration.

DESCRIPTION OF PREFERRED EMBODIMENT

Referring now again to the drawings, there is illustrated a lens positioning device 10 embodying the invention, and as shown in FIG. 1, mounted on a selected one of vertical bars 12 of a slit lamp biomicroscope, for positioning a lens L, such as a 90 diopter lens, in predetermined relationship to the eye of the patient P.

In the embodiment illustrated in FIG. 1, the lens positioning device is secured to the associated vertical bar 12 below the patient head rest 16 and the chin rest 16a, and comprises a clamp means 18 (FIG. 2A) consisting of a generally U-shaped (in plan) member 18a having a generally vertically extending passageway 20 therethrough, open on a side as at 21, of the member 18a, and of size operable to receive therethrough the chin rest vertical bar 12 within the confines of passageway 20. Member 18a has threaded thumb screws 22 coacting therewith which thumb screws are received in threaded relationship with respect to member 18a and pass therethrough into engagement with the vertical bar 12, so as to hold the clamp means in selected stationary position on the vertical bar 12.

Member 18a embodies a flattened surface 24 thereon which preferably coacts with a flat washer 26, and with a coacting base member 28, which in the embodiment illustrated is of generally block-like configuration, with a threaded fastener 30 passing through transverse passage 32 in base member 28 and into threaded coaction with complementary threaded passageway 34 in the clamp member 18a, for selectively tightening and loosening the abutting engagement of the base member 28 and associated washer 26 with the flat or planar area 24 on the clamp member 18a. A wafer spring 36 is preferably provided in a recess 37 formed in the base member 28, and coacts with the headed fastener 30, so as to resist inadvertent loosening of the fastener with respect to the base 28 and clamp member 18a.

A threaded set screw 38 may be provided in the clamp member 18a (FIG. 3) with the set screw extending into the threaded passageway 34 in the clamp member which receives threaded fastener 30, for positively locking the fastener 30 in its selected rotative position, thus insuring that the tension and resistance to relative rotary movement of the base 28 with respect to the clamp member 18a will not change once the desired tension setting is provided by adjustment of the threaded fastener 30.

Mounted on the base member 28 is a first arm 39 with the arm being mounted in through passageway 40 extending generally vertically through the base 28, for rotary movement of the arm 39 relative to base 28.

A collar member 42 is secured to the arm 39 as by means of set screw 44 coacting with the collar 42, and above the base 28, and a handle or cap member 46 coacts with the lower end of arm 39 and may be secured thereto as by means of set screw 48 which passes laterally through the handle member 46 into fixed engagement with the lower end of the arm 39.

A wafer spring 50 may be provided in encircling relation to arm 39, and between the base 28 and the handle 46, so as to provide for adjustment of the tension resistance to rotary movement of the arm 39 about its lengthwise axis and relative to base member 28, by moving the handle 46 toward or away from the base member 28 after of course loosening of the set screw 48 prior to the retightening thereof. This enables the operator-examiner to adapt the rotary movement of the arm 39 relative to its supporting base 28 to the desires of the operator-examiner and after such adjustment and resetting the set screw 48, the tension setting remains constant.

Handle 46 is preferably knurled or roughened as at 52, so as to facilitate the gripping of the handle by the operator-examiner during rotary movement of arm 39 about its lengthwise axis. Upon loosening of the set screw 48 and downward removal of the handle 46 from the lower end of the arm 39, the arm 39 can be lifted upwardly out of its received relationship in passageway 40 in base 28, to dismantle the arm from the base.

Extending laterally from arm 39 and pivotally coupled thereto, is another arm 54, which is adapted to support lens retaining means 56 thereon, as will be hereinafter described in detail.

Arm 54 may be attached by any suitable means, and as illustrated in FIG. 3, to hub 58 of the pivotal connection between arms 39 and 54, with hub 58 receiving therein in threaded relation, a threaded fastener member 60 which passes through an axial passageway 62 in coacting hub 63 and is then received as aforementioned in threaded coaction with complementary threaded hub 58, thus pivotally coupling the arm 54 and attached hub 58 to the arm 39 and attached hub 63. A flat washer member 66 may be provided between hub 63 and hub 58, and a wafer spring 68 may likewise be provided between the hub 63 and the slotted head 69 of fastener 60. It will be seen that by tightening or loosening of the fastener 60, the hub 63 is drawn into tighter or looser relationship with respect to the hub 58, to thus selectively vary the tension and thus the resistance to pivoting between arm 54 and its pivotal connection to arm 39. A set screw 70 extending through a complementary threaded opening in the hub 58 and adapted for engagement with the fastener 60, is adapted to lock the fastener 60 in its selected position, and thus maintain the tension to pivotal movement of the arm 54 with respect to arm 39 that has been selected by the operator-examiner to his or her individual liking.

Arm 54 adjacent its outer end may be provided with a obliquely projecting thickened end portion 72 thereon which in turn mounts a spur 73 having a ball member 73a at its distal end.

The aforementioned lens retaining means 56, in the embodiment illustrated, comprises a split collar 74 which may be formed of any suitable material, such as for instance spring sheet metal, so as to provide the collar with resiliency, and with the split collar being defined by opposing resilient fingers 76, joined at a head portion 78, including generally upstanding spaced ears 78a. Ears 78a are provided with opposing openings 79, therein with the ears being adapted to receive therebetween the aforementioned ball 73a and to movably hold the ball between the coacting openings 79 in the ears, thus movably mounting the lens retaining means to the ball, while permitting universal movement of the lens retaining means 56 with respect to the ball 73a and attaching spur 73.

The spacing between the ears 78a is preferably slightly smaller than the diameter of the ball so that when the ball is received between the ears 78 of the lens retaining means and the periphery of the ball coacts with and extends into the openings 79 in the opposing ears, the ball is gripped by the ears with sufficient frictional engagement that the lens retaining means 56 will remain in whatever position it is placed by the operator-examiner and thus will not pivot freely about the diametrical axis of the ball 73a unless and until force applied by the operator's fingers causes desired positioning movement of the lens retaining means. Thus it will be understood that in whatever position the lens retaining means 56 is placed by the operator-examiner, it tends to remain in that position until it is disturbed by force applied thereto.

A lens retaining ring 80 (FIGS. 3, 4 and 5) of conventional well-known type, and which may be formed of any suitable material, such as for instance metal, or plastic, is adapted to be received between the arcuate, resilient fingers 76 of the lens retaining means 56, and to be held by the lens retaining means 56 in whatever position the lens retaining means is placed by the operator-examiner. The lens retaining ring 80 conventionally has a recessed circumferential slot 82 formed therein which receives the spaced fingers 76 of the lens retaining means 56 in guiding relation, with the fingers 76 being of sufficient length that the distal ends of the fingers are disposed beyond a horizontal plane (with reference to FIG. 3) passing through the axis of lens ring 80. The shoulders 83 defined in part by the slot 82 in ring 80, may be knurled (as illustrated in FIGS. 4 and 5) or otherwise roughened, so as to facilitate rotation by the operator-examiner of the ring 80 and mounted lens L which is received within the confines of the ring 80, for the fundus examination. The distal ends 84 of the fingers 76 preferably diverge outwardly as shown in FIGS. 3, 6 and 7, to facilitate the entry of the lens ring 80 between the resilient fingers and into mounted condition on the lens retaining means 56.

The lens positioning device 10 is adapted to be mounted on the right chin rest vertical bar of the slit lamp biomicroscope (with reference to FIG. 1) so that the thumb screws 22 generally point to the back and middle of the slit lamp table (not shown) and preferably so that the angle of the plane of surface 24 of clamp member 18a at the clamp means 18 is at an angle of approximately 20 degrees with respect to the vertical plane passing through the lengthwise axes of the opposed right and left vertical bars of the biomicroscope, and as diagrammatically illustrated in FIG. 2B. The horizontal arm 54 of the device is adapted to be extended generally parallel to the horizontal when performing a fundus examination, and as illustrated in FIG. 1.

As aforementioned, the spring tension at each joint of the device is adapted to be first adjusted by the operator-examiner to a tension suitable or desirable for his own personal use, and then the respective set screws are tightened so as to lock the tension settings in the selected positions so that they do not vary during the patient examination. The lens retaining ring 80 mounting a lens is then adapted to be inserted into the lens retaining means 56 between the arms 76 thereof, until the arms completely grasp and support the retaining ring. The lens and associated mounting ring 80 may then be moved, positioned and adjusted by holding the lens around the circumference of the retaining ring, to perform the fundus examination in the conventional manner, but without the necessity of manually supporting the lens and mounting ring.

If the lateral, vertical and rotary to-and-fro motions do not seem to satisfy or be appropriate for the particular operator-examiner's liking, such tension settings can be adjusted by loosening the appropriate locking set screw, and rotating the adjustment rotary screw clockwise for tighter motion or counterclockwise for looser motion. Once the proper movement tension has been attained, the set screws can then be tightened to retain such tension settings.

From the foregoing discussion and accompanying drawings, it will be seen that the invention provides a novel lens positioning device for indirect biomicroscopy of the eye comprising a clamp for removably attaching the device to a chin rest vertical bar of a slit lamp biomicroscope, with the lens positioning device including an arm extending upwardly from the clamp, and means for pivoting the arm in a generally vertical plane relative to the clamp, and another arm extending laterally of the first mentioned arm and pivoted thereto, and with lens retaining means adapted to removably receive and mount thereon a lens with the lens retaining means being supported by the other arm and being movably coupled thereto, for enabling ready manual positioning of the lens retaining means relative to the other arm and with the lens retaining means including means operative to cause the lens retaining means to remain where positioned relative to the other arm, until movement force is applied thereto.

The invention also provides a novel lens positioning device for indirect biomicroscopy of the eye wherein a conventional lens ring can be readily inserted into the lens retaining means of the device and readily removed therefrom and when so positioned in the lens retaining means is adapted to be readily adjusted and moved by the operator-examiner without the necessity of manually supporting or holding the lens ring and lens.

The invention also provides a lens positioning device of the aforementioned type which includes means for selectively adjusting the tension movement settings of the pivotal connections between the arms of the device for adjusting the settings to the likes or desires of the operator-examiner or practitioner, and which includes means for locking in the respective tension setting upon the selection thereof.

The terms and expressions which have been used are used as terms of description and not of limitation, and there is no intention in the use of such terms and expressions of excluding any equivalents of any of the features shown or described, or portions thereof, and it is recognized that various modifications are possible within the scope of the invention claimed.

I claim:

1. A lens positioning device for indirect biomicroscopy of the eye comprising clamp means for removably attaching said device to a chin rest vertical bar of a slit-lamp biomicroscope, an arm extending upwardly from said clamp means, means pivoting said arm in a generally vertical plane relative to said clamp means, another arm extending laterally of the first mentioned arm and pivoted thereto, and lens retaining means adapted to removably receive and mount thereon a lens, said lens retaining means being supported by said other arm and being movably coupled thereto for enabling ready manual positioning of said lens retaining means relative to said other arm, and said lens retaining means including means operative to cause said lens retaining means to remain where so positioned relative to said other arm, and wherein said clamp means comprises a member having a generally vertically extending passageway therethrough open on a side of said member and of a size operable to receive therethrough the associated chin rest vertical bar within the confines of said passageway, and adjustable means coacting with said member and with said vertical passageway therethrough for adjustably securing said device to the associated chin rest vertical bar.

2. A device in accordance with claim 1 including means for rotating the first mentioned arm about its lengthwise axis and relative to said clamp means, and upon said rotation causing swinging movement of said other arm and attached lens retaining means in an arc about said lengthwise axis.

3. A device in accordance with claim 1 wherein said lens retaining means is movably coupled to said other arm by a ball secured to said other arm, said means operative to cause said lens retaining means to remain where positioned comprising a socket on said lens retaining means receiving said ball therein in predetermined frictional but movable relationship.

4. A device in accordance with claim 1 wherein said lens retaining means is supported on said other arm by a spur rigidly secured to said other arm and having adjacent its distal end a ball, and a socket joint on said lens retaining means coacting with said ball and thus coupling said lens retaining means to said other arm whereby said lens retaining means is supported for universal movement relative to said other arm, said socket joint coacting in frictional engagement with said ball and providing the means operative.

5. A device in accordance with claim 1 wherein said means for pivoting said first mentioned arm in a general vertical plane comprises a base mounted for pivotal movement in a generally vertical plane about a generally horizontal axis passing through said clamp means, and means for selectively tightening or loosening the tension to permissible pivotal movement of said base relative to said member of said clamp means so as to be able to selectively increase or decrease the resistance to said pivotal movement of said base relative to said member.

6. A device in accordance with claim 5 including means for selectively adjusting the tension for resistance to relative movement of said other arm of said device relative to said first mentioned arm, and other means for locking in said tension upon selection thereof.

7. A device in accordance with claim 5 wherein said member of said clamp means includes a planar surface which is disposed in a generally vertical plane when said device is mounted on the associated chin rest vertical bar, and said base has a planar surface disposed in confronting relative pivotal movement with respect to the first mentioned planar surface, said first mentioned planar surface being disposed in a plane oriented at an angle of approximately 20 degrees from a vertical plane passing through the lengthwise axes of the pair of spaced chin rest vertical bars of an associated biomicroscope and disposed on the examiner's side of the last mentioned vertical plane.

8. A lens positioning device for indirect biomicroscopy of the eye comprising clamp means for removably attaching said device to a chin rest vertical bar of a slit-lamp biomicroscope, an arm extending upwardly from said clamp means, means pivoting said arm in a generally vertical plane relative to said clamp means, another arm extending laterally of the first mentioned arm and pivoted thereto, and lens retaining means adapted to removably receive and mount thereon a lens, said lens retaining means being supported by said other arm and being movably coupled thereto for enabling ready manual positioning of said lens retaining means including means operative to cause said lens retaining means to remain where so positioned relative to said other arm, and wherein said lens retaining means comprises a split collar formed of opposing resilient fingers adapted to receive therebetween a lens retaining ring mounting a lens therein whereby a condensing lens and said associated lens retaining ring can be inserted into and removed from said collar by forcing said fingers apart.

9. A lens positioning device for indirect biomicroscopy of the eye comprising clamp means for removably attaching said device to a chin rest vertical bar of a slit-lamp biomicroscope, an arm extending upwardly from said clamp means, means pivoting said arm in a generally vertical plane relative to said clamp means, another arm extending laterally of the first mentioned arm and pivoted thereto, and lens retaining means adapted to removably receive and mount thereon a lens, said lens retaining means being supported by said other arm and being movably coupled thereto for enabling ready manual positioning of said lens retaining means relative to said other arm, and said lens retaining means including means operative to cause said lens retaining means to remain where so positioned relative to said other arm, and wherein said lens retaining means comprises a split collar defined in part by opposed resilient fingers joined at a head portion which includes generally upstanding spaced ears, each of which has an opening therethrough axially aligned with the corresponding opening in the opposing ear, said other arm having a spur projecting therefrom in a generally diagonally downwardly extending direction and having a ball on the distal end of said spur received between said ears with the exterior periphery of said ball entering said opposing openings in said ears and thus detachably coupling said lens retaining means to said other arm in frictionally coacting and generally universally adjustable relation thereto, said resilient fingers being adapted to detachably receive therebetween an associated lens mounted in a retaining ring for gripping and removably holding the lens and retaining ring on said lens retaining means.

10. A device in accordance with claim 9 wherein said lens retaining means is formed of spring metal.

11. A device in accordance with claim 9 wherein said fingers are arcuately curved and have outwardly divergent end portions, said end portions facilitating the entry of the associated lens retaining ring and lens between said fingers.

* * * * *